(12) United States Patent
Yamaguchi et al.

(10) Patent No.: US 7,981,687 B2
(45) Date of Patent: Jul. 19, 2011

(54) INK COMPOSITION FOR SENSING GAS EXPOSURE AND GAS EXPOSURE INDICATOR

(75) Inventors: Norihiro Yamaguchi, Osaka (JP); Kyoko Sano, Osaka (JP); Hiroshi Inoue, Osaka (JP)

(73) Assignee: Sakura Color Products Corporation, Osaka (JP)

( * ) Notice: Subject to any disclaimer, the term of this patent is extended or adjusted under 35 U.S.C. 154(b) by 0 days.

(21) Appl. No.: 10/594,587

(22) PCT Filed: Mar. 30, 2005

(86) PCT No.: PCT/JP2005/006138
§ 371 (c)(1),
(2), (4) Date: Apr. 22, 2008

(87) PCT Pub. No.: WO2005/095948
PCT Pub. Date: Oct. 13, 2005

(65) Prior Publication Data
US 2008/0267811 A1 Oct. 30, 2008

(30) Foreign Application Priority Data

| Mar. 30, 2004 | (JP) | 2004-101008 |
| Mar. 30, 2004 | (JP) | 2004-101035 |
| May 20, 2004 | (JP) | 2004-150062 |
| May 20, 2004 | (JP) | 2004-150063 |
| Aug. 9, 2004 | (JP) | 2004-232261 |
| Aug. 9, 2004 | (JP) | 2004-232288 |
| Mar. 8, 2005 | (JP) | 2005-064179 |

(51) Int. Cl.
*G01N 33/00* (2006.01)

(52) U.S. Cl. ... 436/135; 436/164; 436/807; 106/163.01; 106/164.41; 106/287.3; 422/28; 422/401; 422/83; 422/86

(58) Field of Classification Search ............... 436/135, 436/164, 807; 106/163.01, 164.41, 287.3; 422/28, 401, 83, 86
See application file for complete search history.

(56) References Cited

U.S. PATENT DOCUMENTS

| 5,955,025 | A | * | 9/1999 | Barrett | 422/28 |
| 6,267,242 | B1 | * | 7/2001 | Nagata et al. | 206/459.1 |
| 6,410,338 | B1 | * | 6/2002 | Lippold et al. | 436/166 |
| 2001/0054374 | A1 | * | 12/2001 | Omatsu et al. | 116/206 |
| 2002/0051733 | A1 | * | 5/2002 | Antonoplos et al. | 422/56 |
| 2005/0054374 | A1 | | 3/2005 | Namiki | |

FOREIGN PATENT DOCUMENTS

| EP | 1312918 A2 * | 5/2003 |
| GB | 2168082 A * | 6/1986 |
| JP | 2001-174449 A | 6/2001 |
| JP | 2002-303618 A | 10/2002 |
| JP | 2003-325646 A | 11/2003 |
| JP | 2004-101488 A | 4/2004 |

OTHER PUBLICATIONS

Japanese Office Action dated Jun. 9, 2010, issued in corresponding Japanese Patent Application No. 2005-064179.

* cited by examiner

*Primary Examiner* — Jill Warden
*Assistant Examiner* — Monique Cole
(74) *Attorney, Agent, or Firm* — Westerman, Hattori, Daniels & Adrian, LLP

(57) ABSTRACT

An object of the present invention is to provide a material for more easily and accurately detecting treatment status using gas exposure. The present invention relates to an ink composition for detecting an oxidizing gas, or the like, comprising at least one type of azo dye, methine dye, triarylmethane dye and thiazine dye.

28 Claims, 2 Drawing Sheets

① Composition A    ② Composition B

① Composition A    ② Composition B

① Composition A    ② Composition B

INK COMPOSITION FOR SENSING GAS EXPOSURE AND GAS EXPOSURE INDICATOR

TECHNICAL FIELD OF THE INVENTION

The present invention relates to an ink composition for detecting gas exposure and a gas exposure detection indicator. More particularly, the present invention relates to an ink composition which changes color as a result of being exposed to an oxidizing gas or plasma hydrogen peroxide atmosphere, and an indicator formed by using the ink composition.

BACKGROUND ART OF THE INVENTION

In addition to sterilizing and disinfecting foods and utensils, Ozone and other oxidizing gases are used to sterilize, disinfect or deodorize predetermined atmospheres such as hospital operating rooms. On the one hand, gases like ozone are extremely toxic and have an effect on the human body. On the other hand, however, the concentration of oxidants in the air is an important element for predicting photochemical smog levels. Consequently, various methods have been developed for monitoring and detecting these oxidizing gas concentrations. For example, a color change based on a reaction of the following formula (1) is primarily used to detect ozone.

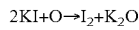

$$2KI + O \rightarrow I_2 + K_2O$$

Examples of conventionally known detection methods using this principle include a method in which a gas containing ozone is introduced into a potassium iodide solution followed by optically measuring the degree of a color change proportional to the amount of iodine formed with a calorimeter, and simpler methods using a detection tube.

In the above-mentioned optical detection method, the measuring method is complicated and a certain amount of time is required until detection. In addition, since the device itself is extremely expensive, huge costs are incurred particularly in the case of attempting to simultaneously measure ozone concentrations at multiple locations since a plurality of devices are required. In addition, in the case of using the above-mentioned detection tube, although the method is simpler than the above-mentioned optical method, it is still expensive, and it is necessary to aspirate oxidant either manually or automatically for each measurement.

Sterilization treatment is carried out for disinfecting and sterilizing various materials and instruments used in hospitals and research facilities. Known examples of this sterilization treatment include high-temperature steam sterilization, ethylene oxide gas sterilization and plasma sterilization treatment. Among these, plasma sterilization treatment sterilizes equipment and materials with low-temperature plasma by generating plasma in a hydrogen peroxide or other oxidizing gas atmosphere, and has the advantage of enabling sterilization at a comparatively low temperature.

In this sterilization treatment as well, it is necessary to install an indicator to confirm whether or not the sterilization treatment has been completed in the same manner as other treatment methods. More specifically, it is necessary to install an indicator for determining the atmospheric gas concentration in the treatment system and exposure time within the plasma sterilization device.

A known example of a technology of the prior art relating to the above-mentioned indicator involves detection of sterilization treatment by a color change from blue to light yellow due to the action of peracetic acid or acetic acid gas by an indicator using a type of pH indicator in the form of bromphenol blue when monitoring a sterilization step in low-temperature plasma sterilization using a gas containing peracetic acid and acetic acid as the main components thereof (Patent Document 1: U.S. Pat. No. 5,482,684).

In addition, a plasma sterilization indicator is known which is composed of a pigment, a coloring assistant and a binder, and changes color as a result of plasma sterilization (Patent Document 2: Japanese Patent Application Publication No. H11-178904, Patent Document 3: Japanese Patent Application Publication No. 2002-11081).

Moreover, an ink composition for detecting plasma sterilization is known which contains an anthraquinone dye having at least one type of amino group among a primary amino group and secondary amino group (Patent Document 4: Japanese Patent Application Publication No. 2001-174449).

DISCLOSURE OF THE INVENTION

However, the indicator of Patent Document 1 has the problem of stability following the color change in that the color following the color change returns to the original color when the indicator is left to stand after undergoing a color change due to sterilization. If the color of the indicator returns to the original color, it becomes unclear as to whether or not materials and equipment placed within a device have undergone sterilization.

In addition, in Patent Documents 2 to 4, there is room for improvement of detection accuracy during hydrogen peroxide plasma sterilization. In the case of treating medical instruments and so forth in a hydrogen peroxide plasma sterilization device in particular, sterilization treatment is carried out with the sterilized materials sealed in a special pouch (pouch made of polyethylene synthetic paper) so as to maintain sterilization even after the sterilized materials are taken out of the device at completion of treatment. Treated materials sealed in the above-mentioned pouch are treated by hydrogen peroxide plasma sterilization through the pouch. In this case, it is necessary to arrange an indicator within the pouch together with the treated material. However, in the case of arranging the indicator within the pouch, the desired color change is no longer observed in the case of a conventional indicator, thereby resulting in the problem of being unable to obtain adequate detection accuracy.

Thus, an object of the present invention is to provide a method enabling simple and accurate detection of a treated state by gas exposure.

More specifically, an object of the present invention is provide a material which enables an oxidizing gas to be detected more easily. In addition, an object of the present invention is to provide an ink composition for detecting hydrogen peroxide plasma sterilization capable of more accurately detecting completion of sterilization treatment even if sealed in a pouch for hydrogen peroxide plasma sterilization, and an indicator for detecting hydrogen peroxide plasma sterilization using said ink composition.

As a result of conducting extensive research to solve the above-mentioned problems of the prior art, the inventors of the present invention found that the above-mentioned objects can be achieved by using an ink composition having a specific composition, thereby leading to completion of the present invention.

Namely, the present invention relates to an ink composition for detecting gas exposure and a gas exposure detection indicator as described below.

1. An ink composition for detecting an oxidizing gas, comprising at least one selected from the group consisting of azo dye, methine dye, triarylmethane dye and thiazine dye.

2. The ink composition for detecting an oxidizing gas according to above 1, which further comprises a cationic surfactant.

3. The ink composition for detecting an oxidizing gas according to above 2, wherein the cationic surfactant is at least one selected from the group consisting of an alkyl trimethyl ammonium salt, isoquinolinium salt, imidazolinium salt and pyridinium salt.

4. The ink composition for detecting an oxidizing gas according to above 1, which further comprises at least one selected from the group consisting of extender and resin binder.

5. The ink composition for detecting an oxidizing gas according to above 1, which further comprises at least one type of colorant which does not change color in an oxidizing gas atmosphere.

6. The ink composition for detecting an oxidizing gas according to above 1, which further comprises an anthraquinone dye as a dye.

7. An oxidizing gas detection indicator, comprising a color changing layer formed of the ink composition according to above 1.

8. The oxidizing gas detection indicator according to above 7, which further comprises a non-color changing layer which does not change color in an oxidizing gas atmosphere.

9. An ink composition for detecting hydrogen peroxide plasma sterilization, comprising: 1) at least one selected from the group consisting of azo dye, methine dye and anthraquinone dye, 2) a nitrogen-containing polymer, and 3) a cationic surfactant.

10. The ink composition according to above 9, wherein all or a portion of the nitrogen-containing polymer is a polyamide resin.

11. The ink composition according to above 10, wherein the polyamide resin is a reaction product of a dimer of linoleic acid and a di- or polyamine.

12. The ink composition according to above 9, wherein the cationic surfactant is at least one selected from the group consisting of an alkyl trimethyl ammonium salt, isoquinolinium salt, imidazolinium salt and pyridinium salt.

13. The ink composition according to above 9, which further comprises at least one selected from the group consisting of extender and resin binder.

14. The ink composition according to above 13, wherein all or a portion of the resin binder is a cellulose resin.

15. The ink composition according to above 13, wherein all or a portion of the extender is silica.

16. The ink composition according to above 9, wherein the content of the nitrogen-containing polymer is 1 to 20% by weight of the ink composition.

17. The ink composition according to above 9, which further comprises at least one type of colorant which does not change color in a plasma sterilization treatment atmosphere.

18. The ink composition according to above 9, which further comprises at least one type of component which changes color by reacting with hydrogen peroxide.

19. The ink composition according to above 18, wherein the component which changes color by reacting with hydrogen peroxide contains ammonium aurintricarboxylate.

20. The ink composition according to above 9, which further comprises at least one type of organic amine.

21. An indicator for detecting hydrogen peroxide plasma sterilization, comprising a color changing layer formed of the ink composition according to above 9.

22. The indicator according to above 21, which has a plurality of cracks in the surface of the color changing layer.

23. The indicator according to above 21, which further comprises a non-color changing layer which does not change color in a plasma sterilization treatment atmosphere.

24. The indicator according to above 21, which further comprises a colored layer which changes color in a hydrogen peroxide atmosphere.

25. The indicator according to above 24, wherein the colored layer and the color changing layer are formed so as to be mutually overlapping.

26. The indicator according to above 25, wherein the colored layer and the color changing layer are formed in a linear or spotted pattern so as not to be mutually overlapping.

27. A pouch for hydrogen peroxide plasma sterilization provided with the indicator according to above 21 on an inner surface of a gas-permeable pouch.

28. The pouch according to above 27, which is provided with a transparent window in a portion of the pouch so as to allow visual confirmation of the indicator from the outside.

29. The pouch according to above 27, wherein the gas-permeable pouch is formed from polyethylene fibers.

30. A hydrogen peroxide plasma sterilization treatment method, comprising the steps of loading a treated material into the pouch according to above 21, sealing the pouch with the treated material loaded therein, and placing the pouch in a hydrogen peroxide plasma sterilization atmosphere.

31. The method according to above 30, wherein the pouch is placed in the hydrogen peroxide plasma sterilization atmosphere until the color changing layer of the indicator changes color.

32. A method for confirming hydrogen peroxide plasma sterilization treatment, comprising the steps of loading a treated material into the pouch according to claim 21, sealing the pouch with the treated material sealed therein, placing the pouch in a hydrogen peroxide plasma sterilization atmosphere, and confirming a color difference in the indicator of the pouch.

ADVANTAGES OF THE INVENTION

The ink composition for detecting gas exposure and the gas exposure detection indicator of the present invention offer the advantages indicated below.

(1) Since the ink composition and indicator for detecting an oxidizing gas of the present invention contain at least one type of an azo dye, methine dye, triarylmethane dye and thiazine dye as a detecting component thereof, the ink composition and indicator of the present invention have superior stability without returning to the original color after changing color, and are able to reliably detect that oxidizing gas treatment has been carried out. In addition, detection sensitivity, color change rate and so on can be controlled as desired by changing the type and blending ratio of the aforementioned azo dye.

(2) The ink composition for detecting an oxidizing gas of the present invention can also be used for printing, writing or stamping by blending with a resin binder and so on, and can be used by coating onto a base material such as paper or film.

(3) The indicator for detection of an oxidizing gas of the present invention can be reliably distinguished by a color change in the case of forming a non-color changing layer. Moreover, if composed in the form of a sheet or plate as the whole shape, space can be conserved and selection of the base material can be given greater flexibility, enabling it to be installed anywhere.

(4) The indicator for detecting an oxidizing gas of the present invention can express a pattern, characters or symbols and so on corresponding to the purpose of use by suitably combining a color changing layer and a non-color changing layer, enabling it to impart superior design qualities and allowing it to be used in a wide range of applications.

(5) Detection with high sensitivity can be realized in the case of using a cationic surfactant in the indicator for detecting an oxidizing gas of the present invention in particular. Detection sensitivity, color change rate and so on can be controlled as desired by changing the types and blending ratios of components such as this cationic surfactant and extender, thereby making it possible to carry out quantitative measurements.

(6) Since the ink composition and indicator for detecting hydrogen peroxide sterilization of the present invention contain a specific dye and nitrogen-containing polymer, a desired color change effect can be obtained even within a pouch for hydrogen peroxide plasma sterilization treatment. Higher detection sensitivity can be achieved in the case of using a polyamide resin for the nitrogen-containing polymer in particular.

(7) In addition, in the case of using silica as an extender, cracks can be effectively formed in the surface of the color changing layer, thereby making it possible to further contribute to improvement of detection sensitivity.

(8) The ink composition for detecting hydrogen peroxide plasma sterilization of the present invention can also be used for printing, writing or stamping by blending with a resin binder and so on, and can be used by coating onto a base material such as paper or film. In the case of using a cellulose resin for the resin binder in particular, since adequate fixation can be obtained even if cracks are formed in a color changing layer by blending with silica and so forth, situations in which the color changing layer separates or falls from the base material can be prevented in advance.

(9) Since the indicator for detecting hydrogen peroxide plasma sterilization of the present invention is provided with a color changing layer according to the ink composition of the present invention, it can be preferably used for hydrogen peroxide plasma sterilization treatment.

(10) The pouch of the present invention makes it possible to accurately determine completion of sterilization treatment since the indicator of the present invention has the ability to detect said completion even within a pouch in the case a treated material is placed in the pouch and sealed therein followed by placing the pouch together with the material in a hydrogen peroxide plasma sterilization atmosphere.

BEST MODE FOR CARRYING OUT THE INVENTION

Figure 1:
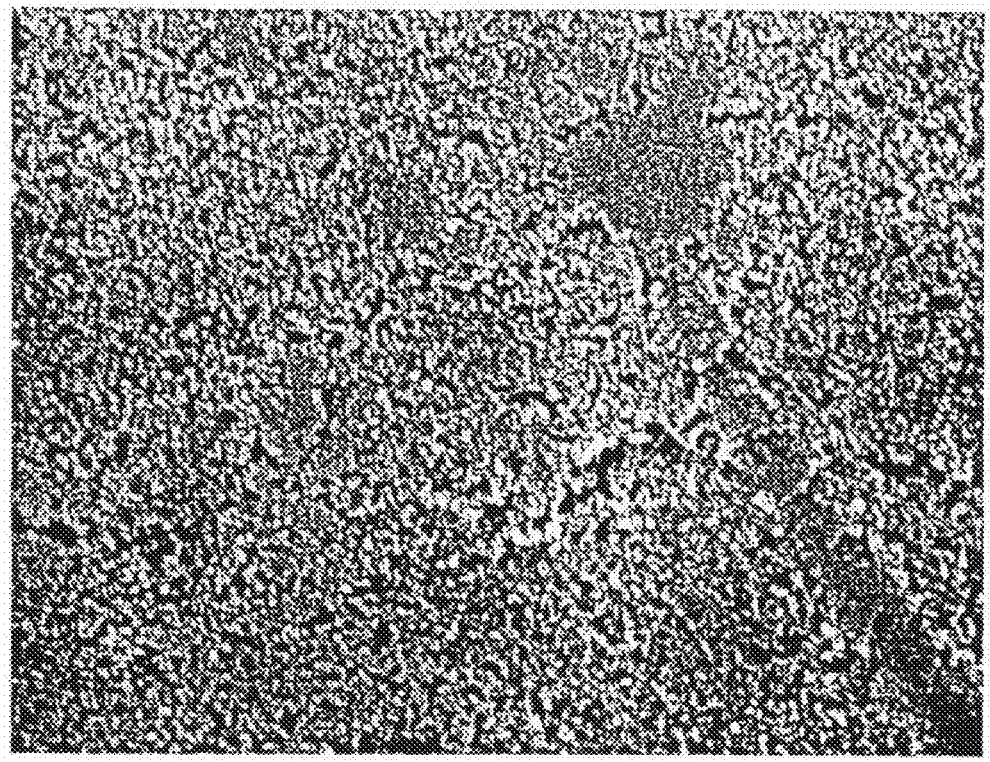
FIG. 1 is a photograph showing the results of observing a surface coated with the ink composition of Example 1 with a scanning electron microscope.

<First Invention>
(1) Ink Composition for Detecting Oxidizing Gas

The ink composition for detecting oxidizing gas of the present invention comprises at least one type of azo dye, methine dye, triarylmethane dye and thiazine dye (to be referred to as a "dye of the present invention").

There are no limitations on the azo dye provided it has an —N=N— azo group for the chromophore, examples of which include monoazo dyes, polyazo dyes, metal complex salt azo dyes, stilbene azo dyes and thiazole azo dyes. Specific examples of azo dyes represented in terms of the dye numbers thereof include C.I. Disperse Red 13, C.I. Disperse Red 52, C.I. Disperse Violet 24, C.I. Disperse Blue 44, C. I. Disperse Red 58, C.I. Disperse Red 88, C.I. Disperse Yellow 23, C.I. Disperse Orange 1, C.I. Disperse Orange 5, C.I. Solvent Red 1, C. I. Solvent Red 3 and C.I. Solvent Red 23. One type or two or more types can be used.

The methine dye may be any dye which has a methine group. Thus, the present invention includes methine dyes such as polymethine dyes and cyanine dyes. These can be suitably selected from known or commercially available methine dyes, specific examples of which include C.I. Basic Red 12, C.I. Basic Red 13, C.I. Basic Red 14, C.I. Basic Red 15, C.I. Basic Red 27, C.I. Basic Red 35, C.I. Basic Red 36, C.I. Basic Red 37, C.I. Basic Red 45, C.I. Basic Red 48, C.I. Basic Yellow 11, C.I. Basic Yellow 12, C.I. Basic Yellow 13, C.I. Basic Yellow 14, C.I. Basic Yellow 21, C.I. Basic Yellow 22, C.I. Basic Yellow 23, C.I. Basic Yellow 24, C.I. Basic Violet 7, C.I. Basic Violet 15, C.I. Basic Violet 16, C.I. Basic Violet 20, C.I. Basic Violet 21, C.I. Basic Violet 39, C.I. Basic Blue 62, and C.I. Basic Blue 63. One type or two or more types may be used.

There are no limitations on the triarylmethane dye, and a known or commercially triarylmethane dye can be used, examples of which include C.I. Basic Blue 1, C.I. Basic Blue 26, C.I. Basic Blue 5, C.I. Basic Blue 8, C.I. Basic Green 1, C.I. Basic Red 9, C.I. Basic Violet 12, C.I. Basic Violet 14, C.I. Basic Violet 3, C.I. Solvent Green 15 and C.I. Solvent Violet 8. One type or two or more types may be used. Among these triarylmethane dyes, C.I. Solvent Violet 8, C.I. Basic Green 1, C.I. Basic Red 9 and C.I. Basic Blue 1 can be used preferably.

There are no particular limitations on the thiazine dye, and a known or commercially available thiazine dye can be selected, examples of which include C.I. Basic Blue 9, C.I. Basic Blue 25, C.I. Basic Blue 24, C.I. Basic Blue 17, C.I. Basic Green 5 and C.I. Solvent Blue 8. One type or two or more types may be used. Among these thiazine dyes, C.I. Basic Blue 9 can be used preferably.

Although varying according to the type of dye used, desired detection characteristics and so forth, the content of a dye of the present invention is from 0.01 to 10% by weight, preferably from 0.05 to 5% by weight, and more preferably from 0.1 to 2% by weight of the ink composition.

In the present invention, a dye other than a dye of the present invention, or a pigment, may be used in combination with a dye of the present invention. For example, an anthraquinone dye can be used in combination with a dye of the present invention. There are no particular limitations on the anthraquinone dye provided it has the basic chemical structure of anthraquinone, and known anthraquinone disperse dyes and so on can also be used.

Specific examples of anthraquinone dyes include 1,4-diaminoanthraquinone (C.I. Disperse Violet 1), 1-amino-4-hydroxy-2-methoxyanthraquinone (C.I. Disperse Red 4), 1-amino-4-methylaminoanthraquinone (C.I. Disperse Violet 4), 1,4-diamino-2-methoxyanthraquinone (C.I. Disperse Red 11), 1-amino-2-methylanthraquinone (C.I. Disperse Orange 11), 1-amino-4-hydroxyanthraquinone (C.I. Disperse Red 15), 1,4,5,8-tetraminoanthraquinone (C.I. Disperse Blue 1) and 1,4-diamino-5-nitroanthraquinone (C.I. Disperse Violet 8). Other known examples of dyes that can be used include C.I. Solvent Blue 14, C.I. Solvent Blue 63, C.I. Solvent Violet 13, C.I. Solvent Violet 14, C.I. Solvent Red 52, C.I. Solvent Red 114, C.I. Vat Blue 21, C.I. Vat Blue 30, C.I. Vat Violet 15, C.I. Vat Violet 17, C.I. Vat Red 19, C.I. Vat Red 28, C.I. Acid Blue 23, C.I. Acid Blue 80, C.I. Acid Violet 43, C.I. Acid Violet 48, C.I. Acid Red 81, C.I. Acid Red 83, C.I. Reactive Blue 4, C.I. Reactive Blue 19 and C.I. Disperse Blue 7. These anthraquinone dyes can be used alone or in a combination of two or more types. Among these anthraquinone dyes, C.I. Disperse Blue 7 and C.I. Disperse Violet 1 are preferable. In addition, in the present invention, detection sensitivity can be controlled by changing the types (e.g., molecular structure) of these anthraquinone dyes.

Although there are no limitations on the content of anthraquinone dye, it is preferably 0.01 to 10% by weight, and particularly preferably 0.05 to 5% by weight, of the ink composition.

In the present invention, other dyes or pigments may also be present. In particular, the present invention may contain a pigment component which does not change color in an oxidizing gas treatment atmosphere (to be referred to as a non-color changing pigment). As a result, visual effects resulting from changing from a certain color to a different color can be further enhanced. Known inks (ordinary colored inks) can be used for the non-color changing pigment. The content of the non-coloring changing pigment in this case may be suitably set corresponding to the type of non-color changing pigment and so on.

The ink composition of the present invention preferably also contains a cationic surfactant.

Although there are no particular limitations on the cationic surfactant, in particular at least one type of alkyl ammonium salt, isoquinolinium salt, imidazolinium salt and pyridinium salt can be used. These known or commercially available cationic surfactants can also be used. In the present invention, combining the use of these cationic surfactants with the dye of the present invention makes it possible to obtain even more superior detection sensitivity.

Among alkyl ammonium salts, alkyl trimethyl ammonium salts and dialkyl dimethyl ammonium salts are preferable, specific examples of which include palm alkyl trimethyl ammonium chloride, beef tallow alkyl trimethyl ammonium chloride, behenyl trimethyl ammonium chloride, hexadecyl trimethyl ammonium chloride, lauryl trimethyl ammonium chloride, octadecyl trimethyl ammonium chloride, dioctyl dimethyl ammonium chloride, distearyl dimethyl ammonium chloride and alkylbenzyl dimethylammonium chloride. Palm alkyltrimethyl ammonium chloride and lauryl trimethyl ammonium chloride are particularly preferable.

Examples of isoquinolinium salts include lauryl isoquinolinium bromide, cetyl isoquinolinium bromide, cetyl isoquinolinium chloride and lauryl isoquinolinium chloride, with lauryl isoquinolinium chloride being particularly preferable.

Examples of imidazolinium salts include 1-hydroxyethyl-2-oleylimidazolinium chloride and 2-chloro-1,3-dimethylimidazolinium chloride, with 2-chloro-1,3-dimethylimidazolinium chloride being particularly preferable.

Examples of pyridinium salts include pyridinium chloride, 1-ethylpyridinium bromide, hexadecylpyridinium chloride, cetylpyridinium chloride, 1-butylpyridinium chloride, N-n-butylpyridinium chloride, hexadecylpyridinium bromide, N-hexadecylpyridinium bromide, 1-dodecylpyridinium chloride, 3-methylhexylpyridinium chloride, 4-methylhexylpyridinium chloride, 3-methyloctylpyridinium chloride, 2-chloro-1-methylpyridinium iodide, 3,4-dimethylbutylpyridinium chloride, pyridinium-n-hexadecyl chloride hydrate, N-(cyanomethyl)pyridinium chloride, N-acetonylpyridinium bromide, 1-(aminoformylmethyl)pyridinium chloride, 2-amidinopyridinium chloride, 2-aminopyridinium chloride, N-aminopyridinium iodide, 1-aminopyridinium iodide, 1-acetonylpyridinium chloride and N-acetonylpyridinium bromide, with hexadecylpyridinium chloride being particularly preferable.

Although varying according to the type of cationic surfactant used and so on, the content of cationic surfactant is preferably from 0.2 to 30% by weight, and particularly preferably from 0.5 to 10% by weight, of the ink composition of the present invention.

In the ink composition of the present invention, known components used in inks, such as resin binders, extenders and solvents, can be suitably blended as necessary.

The resin binder may be suitably selected corresponding to the type of base material and so on, and known resin components used in ink compositions for writing, printing and so on can be used without modification, specific examples of which include maleic acid resins, amide resins, ketone resins, alkylphenol resins, rosin-modified resins, polyvinyl butyral, polyvinyl pyrrolidone, cellulose resins, polyester resins, styrene-maleic acid resins, styrene-acrylic acid resins and acrylic resins.

Although the content of resin binder can be suitably set according to the type of resin binder used, desired ink characteristics and so on, the content of resin binder is preferably 50% by weight or less, and particularly preferably 5 to 35% by weight, of the ink composition of the present invention.

There are no particular limitations on the extender, and examples include bentonite, activated clay, aluminum oxide and silica. Other materials known to be used as body pigments can also be used. Porous materials are preferable, and silica is particularly preferable. The addition of such extenders makes it possible to mainly enhance detection sensitivity.

Although varying according to the type of extender used and so on, the content of extender is preferably from 1 to 30% by weight, and particularly preferably from 2 to 20% by weight, of the ink composition of the present invention.

Any solvent can be used for the solvent able to be used in the present invention provided it is normally used in ink compositions for printing, writing and soon, examples of which include alcohol solvents, ester solvents, ether solvents, ketone solvents and hydrocarbon solvents, and the solvent may be suitably selected corresponding to the type of dye used, solubility of the resin binder and so on.

The content of solvent may be suitably adjusted so as to form a remainder after having removed components other than the solvent from the ink composition of the present invention.

Each of these components may be blended simultaneously or sequentially, and uniformly mixed by using a known agitator such as a homogenizer or dissolver. For example, a dye of the present invention, and as necessary, a cationic surfactant, resin binder, extender and so on, may be blended in order into a solvent followed by mixing and stirring with an agitation device.

(2) Oxidizing Gas Detection Indicator

An oxidizing gas detection indicator of the present invention contains a color changing layer composed of the above-mentioned ink composition. In general, the color changing layer can be suitably formed on a base material.

There are no particular limitations on the base material provided it allows the formation of the color changing layer, examples of which include metal/alloy, wood, paper, ceramics, glass, concrete, plastics, textiles (suchasnon-wovenfabric, woven fabric and other fiber sheets) and composite thereof.

The color changing layer in the present invention includes not only that in which the color thereof changes to another color, but also that in which the color fades or disappears.

Formation of the color changing layer can be carried out in accordance with known printing methods such as silk screen printing, gravure printing, offset printing, relief printing and flexography using the ink composition of the present invention. In addition, the color changing layer can also be formed by another method. For example, the color changing layer can be formed by immersing a base material in the ink composition. This is particularly suitable for ink-penetrable materials such as paper and non-woven fabric.

In the present invention, a non-color changing layer which does not change color in an oxidizing gas atmosphere may also be formed on the base material and/or color changing layer. The non-color changing layer can normally be formed from commercially available ordinary colored ink. For example, water-based ink, oil-based ink or non-solvent ink can be used. Components such as resin binders, extenders and solvents blended into known inks may also be contained in the ink used to form the non-color changing layer.

Formation of the non-color changing layer may be carried out in the same manner as in the case of the color changing layer. For example, the non-color changing layer can be formed in accordance with known printing methods such as silk screen printing, gravure printing, offset printing, relief printing and flexography using ordinary colored ink. Furthermore, there are no particular limitations on the order in which the color changing layer and non-color changing layer are printed, and the order may be suitably selected corresponding to the printed design and so on.

In the indicator of the present invention, one layer each of the color changing layer and the non-color changing layer may be formed, or multiple layers of each may be formed. In addition, multiple color changing layers may be laminated together or multiple non-color changing layers may be laminated together. In this case, the laminated color changing layers may have the same or different compositions. Similarly, multiply laminated non-color changing layers may also have the same or different compositions.

Moreover, the color changing layer and the non-color changing layer may be formed entirely or partially over the surface of the base material or each layer. In these cases, it is preferable that the color changing layer and non-color changing layer be formed so that a portion or all of at least one color changing layer is exposed to the oxidizing gas treatment atmosphere to ensure that the color of the color changing layer changes in particular.

In the present invention, the color changing layer and the non-color changing layer may be combined in any manner provided completion of oxidizing gas treatment is able to be confirmed. For example, the color changing layer and non-color changing layer may be formed so that the color difference between the color changing layer and non-color changing layer only be able to be distinguished by a color change of the color changing layer, or they may be formed so that the color difference between the color changing layer and non-color changing layer only disappears when the color of the color changing layer changes. In the present invention, the color changing layer and the non-color changing layer are preferably formed so that the color difference between them can be distinguished only after a color change of the color changing layer.

In the case of allowing a color difference to be distinguished, the color changing layer and non-color changing layer may be formed so that, for example, at least one type of character, pattern or symbol appears when the color changing layer changes color. In the present invention, characters, patterns and symbols include all information indicating that color has changed. These characters and so on may be suitably designed corresponding to the purpose of use and so on.

In addition, mutually different colors may be used for the color changing layer and non-color changing layer prior to changing color. For example, both layers may be made to have substantially the same color, and the color difference (contrast) between the color changing layer and non-color changing layer may be allowed to be distinguished only after the color has changed.

In the indicator of the present invention, the color changing layer and non-color changing layer can be formed so that they do not overlap. As a result, the amount of ink used can be conserved.

Moreover, in the present invention, a color changing layer or non-color changing layer may be additionally formed on at least one of the color changing layer and non-color changing layer. For example, if a color changing layer having a different design is further formed on a layer in which a color changing layer and non-color changing layer are formed so as not to overlap ("color changing-non-color changing layer"), since a state can be created in which the boundary between the color changing layer and non-color changing layer in the color changing-non-color changing layer cannot be substantially distinguished, more superior design properties can be achieved.

The indicator of the present invention can be applied in the case of detecting an oxidizing gas. In particular, examples of oxidizing gases include ozone, hydrogen peroxide, ethylene oxide, nitrogen oxide, or the like. When the indicator of the present invention is exposed to these gases, the dye of the present invention reacts causing it to change color. Thus, when using this indicator, it is exposed to an oxidizing gas atmosphere together with instruments and materials subjected to sterilization or disinfection with oxidizing gas by placing the indicator of the present invention in, for example, a commercially available oxidizing gas treatment device. In this case, a predetermined treatment by the oxidizing gas can be determined to have been carried out by a color change in the color changing layer of the indicator placed in the device.

<Second Invention>

(1) Ink Composition for Detecting Hydrogen Peroxide Plasma Sterilization

The ink composition for detecting hydrogen peroxide plasma sterilization of the present invention comprises: 1) at least one type of anthraquinone dye, azo dye and methine dye, 2) a nitrogen-containing polymer, and 3) a cationic surfactant.

Colorant

In the composition of the present invention, at least one type of anthraquinone dye, azo dye and methine dye is used as a colorant (color changing pigment).

There are no limitations on the anthraquinone dye provided it has the basic chemical structure of anthraquinone, and known anthraquinone dispersion dyes and so on can be used. Anthraquinone dyes having an amino group are particularly preferable. Anthraquinone dyes having at least one primary amino group or secondary amino group are even more preferable. In this case, the anthraquinone dye may have two or more of each group, and the groups may be mutually the same or different.

Specific examples of anthraquinone dyes include 1,4-diaminoanthraquinone (C.I. Disperse Violet 1), 1-amino-4-hydroxy-2-methylaminoanthraquinone (C.I. Disperse Red 4), 1-amino-4-methylaminoanthraquinone (C.I. Disperse Violet 4), 1,4-diamino-2-methoxyanthraquinone (C.I. Disperse Red 11), 1-amino-2-methylanthraquinone (C.I. Disperse Orange 11), 1-amino-4-hydroxyanthraquinone (C.I. Disperse Red 15), 1,4,5,8-tetraminoanthraquinone (C.I. Disperse Blue 1) and 1,4-diamino-5-nitroanthraquinone (C.I. Disperse Violet 8) (parentheses indicate dye numbers). Other known dyes can also be used, examples of which include C.I. Solvent Blue 14, C.I. Solvent Blue 35, C.I. Solvent Blue 63, C.I. Solvent Violet 13, C.I. Solvent Violet 14, C.I. Solvent Red 52, C.I. Solvent Red 114, C.I. Vat Blue 21, C.I. Vat Blue 30, C.I. Vat Violet 15, C.I. Vat Violet 17, C.I. Vat Red 19, C.I. Vat Red 28, C.I. Acid Blue 23, C.I. Acid Blue 80, C.I. Acid Violet 43, C.I. Acid Violet 48, C.I. Acid Red 81, C.I. Acid Red 83, C.I. Reactive Blue 4, C.I. Reactive Blue 19 and C.I. Disperse Blue 7. These anthraquinone dyes may be used alone or in a combination of two or more types. Among these anthraquinone dyes, C.I. Disperse Blue 7 and C.I. Disperse Violet 1 are particularly preferable. In addition, in the present invention, detection sensitivity can also be controlled by changing the types of these anthraquinone dyes (molecular structure and so on).

There are no limitations on the azo dye provided it has one or more —N═N— azo groups as the chromophore, examples of which include monoazo dyes, polyazo dyes, metal complex salt azo dyes, stilbene azo dyes and thiazole azo dyes. Specific examples of azo dyes represented in terms of the dye numbers thereof include C.I. Solvent Red 1, C.I. Solvent Red 3, C.I. Solvent Red 23, C.I. Disperse Red 13, C.I. Disperse Red 52, C.I. Disperse Violet 24, C.I. Disperse Blue 44, C. I. Disperse Red 58, C.I. Disperse Red 88, C.I. Disperse Yellow 23, C.I. Disperse Orange 1 and C.I. Disperse Orange 5. One type or two or more types can be used.

The methine dye may be any dye which has one or more methine group. Thus, the present invention includes methine dyes such as polymethine dyes and cyanine dyes. Moreover, these can be suitably selected from known or commercially available methine dyes, specific examples of which include C.I. Basic Red 12, C.I. Basic Red 13, C.I. Basic Red 14, C.I. Basic Red 15, C.I. Basic Red 27, C.I. Basic Red 35, C.I. Basic Red 36, C.I. Basic Red 37, C.I. Basic Red 45, C.I. Basic Red 48, C.I. Basic Yellow 11, C.I. Basic Yellow 12, C.I. Basic Yellow 13, C.I. Basic Yellow 14, C.I. Basic Yellow 21, C.I. Basic Yellow 22, C.I. Basic Yellow 23, C.I. Basic Yellow 24, C.I. Basic Violet 7, C.I. Basic Violet 15, C.I. Basic Violet 16, C.I. Basic Violet 20, C.I. Basic Violet 21, C.I. Basic Violet 39, C.I. Basic Blue 62, and C.I. Basic Blue 63. One type or two or more types may be used.

Although the content of the above-mentioned colorants can be suitably determined corresponding to the type of colorant, desired hue and so on, in general, the content is preferably about from 0.05 to 5% by weight, and particularly preferably from 0.1 to 1% by weight, of the composition of the present invention.

A dye or pigment other than the above-mentioned colorants may also be present in the present invention. In particular, a pigment component which does not change color in a hydrogen peroxide plasma sterilization treatment atmosphere (non-color changing pigment) may also be contained. As a result, visual effects resulting from changing from a certain color to a different color can be further enhanced. Known inks (ordinary colored inks) can be used for the non-color changing pigment. The content of the non-coloring changing pigment in this case may be suitably set corresponding to the type of non-color changing pigment and so on.

In addition, at least one type of component which changes color in response to hydrogen peroxide may also be contained in the composition of the present invention.

A component which changes color in response to hydrogen peroxide refers to a component which changes color by reacting to hydrogen peroxide prior to plasma generation. In the present invention, a pH indicator can be suitably used, examples of which include ammonium aurintricarboxylate, hematoxin, bromphenol red, neutral red and thymol blue.

In addition, the composition of the present invention preferably contains at least one type of organic amine. Although it is typically not easy to introduce two types of pigments into a single composition and allow them to each demonstrate independent functions without interacting, the addition of an organic amine enables the two functions to be demonstrated independently. Namely, a composition can be made to have both the function of responding to a hydrogen gas atmosphere prior to generation of plasma, and the function of responding to an atmosphere in which plasma has been generated from the hydrogen peroxide. Since organic amines maintain the alkalinity of the composition or coated layer thereof, it is useful for the color change of a pH indicator when contacted by hydrogen peroxide.

There are no particular limitations on the organic amine, and at least one type of primary amine, secondary amine or tertiary amine can be used, specific examples of which include monotriethanol amine, diethanol amine, triethanol amine, isopropyl amine, 3-ethoxypropyl amine and cetyl amine.

Nitrogen-Containing Polymer

A synthetic resin such as a polyamide resin, polyimide resin, polyacrylonitrile resin, amino resin, polyacrylamide, polyvinyl pyrrolidone, polyvinyl imidazole and polyethylene imine can be used for the nitrogen-containing polymer used in the composition of the present invention. One type or two or more types of these synthetic resins can be used. In the composition of the present invention, the nitrogen-containing polymer fulfills the role of a sensitivity enhancer. Namely, the use of a sensitivity enhancer makes it possible to further enhance the detection accuracy (sensitivity) of hydrogen peroxide plasma sterilization. As a result, since color changes reliably even within a pouch or bag for hydrogen peroxide plasma sterilization, the present invention is extremely useful as an indicator used in such a pouch or bag.

From this perspective, a polyamide resin can be used particularly preferably in the present invention. There are no particular limitations on the type or molecular weight of the polyamide resin, and known or commercially available polyamide resins can be used. Polyamide resins which are the reaction products (long-chain linear polymers) of a dimer of linoleic acid and a di- or polyamine can be used particularly preferably. Polyamide resins are thermoplastic resins having a molecular weight of 4000 to 7000, and commercially available products can be used for such resins as well.

Although the content of the nitrogen-containing polymer can be suitably determined corresponding to the type of the above-mentioned polymer, the type of colorant used and so on, in general, it is preferably about from 0.1 to 50% by weight, and particularly preferably from 1 to 20% by weight, of the ink composition of the present invention.

Cationic Surfactant

The ink composition of the present invention also contains a cationic surfactant. Although there are no particular limitations on the cationic surfactant, at least one type of alkyl ammonium salt, isoquinolinium salt, imidazolinium salt and pyridinium salt can be used particularly preferably. Known or commercially available cationic surfactants can also be used. In the present invention, combining the use of these cationic surfactants with the above-mentioned colorants makes it possible to obtain even more superior detection sensitivity.

Among alkyl ammonium salts, alkyl trimethyl ammonium salts and dialkyldimethylammonium salts are preferable, specific examples of which include palm alkyl trimethyl ammonium chloride, beef tallow alkyl trimethyl ammonium chloride, behenyl trimethyl ammonium chloride, hexadecyl trimethyl ammonium chloride, lautyl trimethyl ammonium chloride, octadecyl trimethyl ammonium chloride, dioctyl dimethyl ammonium chloride, distearyl dimethyl ammonium chloride and alkylbenzyl dimethylammonium chloride. Palm alkyl trimethyl ammonium chloride and lauryl trimethyl ammonium chloride are particularly preferable.

Examples of isoquinolinium salts include lauryl isoquinolinium bromide, cetyl isoquinolinium bromide, cetyl isoquinolinium chloride and lauryl isoquinolinium chloride, with lauryl isoquinolinium chloride being particularly preferable.

Examples of imidazolinium salts include 1-hydroxyethyl-2-oleylimidazolinium chloride and 2-chloro-1,3-dimethylimidazolinium chloride, with 2-chloro-1,3-dimethylimidazolinium chloride being particularly preferable.

Examples of pyridinium salts include pyridinium chloride, 1-ethylpyridinium bromide, hexadecylpyridinium chloride, cetylpyridinium chloride, 1-butylpyridinium chloride, N-n-butylpyridinium chloride, hexadecylpyridinium bromide, N-hexadecylpyridinium bromide, 1-dodecylpyridinium chloride, 3-methylhexylpyridinium chloride, 4-methylhexylpyridinium chloride, 3-methyloctylpyridinium chloride, 2-chloro-1-methylpyridinium iodide, 3,4-dimethylbutylpyridinium chloride, pyridinium-n-hexadecyl chloride monohydrate, N-(cyanomethyl)pyridinium chloride, N-acetonylpyridinium bromide, 1-(aminoformylmethyl)pyridinium chloride, 2-amidinopyridinium chloride, 2-aminopyridinium chloride, N-aminopyridinium iodide, 1-aminopyridinium iodide, 1-acetonylpyridinium chloride and N-acetonylpyridinium bromide, with hexadecylpyridinium chloride being particularly preferable.

Although the content of cationic surfactant can be suitably determined according to the type of the above-mentioned cationic surfactant used, type of colorant used and so on, in general, it is about 0.2 to 10% by weight, and particularly preferably 0.5 to 5% by weight, of the composition of the present invention.

Resin Binder, Extender and Other Components

Resin binders, extenders, solvents, leveling agents, antifoaming agents, ultraviolet absorbers, surface adjusters and other known components used in inks can be suitably blended into the ink composition of the present invention as necessary.

A resin binder may be suitably selected corresponding to the type of base material and so on, and known resin components used in ink compositions for writing or printing, for example, can be used without modification, specific examples of which include maleic acid resins, ketone resins, alkylphenol resins, rosin-modified resins, polyvinyl butyral, cellulose resins, polyester resins, styrene-maleic acid resins, styrene-acrylic acid resins and acrylic resins. In the present invention, a cellulose resin can be used particularly preferably. By using a cellulose resin, superior fixation can be obtained even if an extender (such as silica) is contained, thereby making it possible to effectively prevent falling and separation of components from the base material.

Effectively forming a plurality of cracks in a coated surface of an ink composition makes it possible to contribute to improved indicator sensitivity.

Although the content of the resin binder can be suitably determined corresponding to the type of resin binder, type of colorant used and so on, in general, it is preferably about 50% by weight or less, and particularly preferably from 5 to 35% by weight, of the composition of the present invention.

There are no particular limitations on the extender, and examples include bentonite, activated clay, aluminum oxide, silica and silica gel. Other materials known to be used as body pigments can also be used. In particular, at least one type of silica, silica gel and alumina is preferable, with silica being particularly preferable. In the case of using silica and so on, a plurality of cracks can be effectively formed in the surface of the color changing layer in particular. As a result, the detection sensitivity of the indicator can be further enhanced.

Although the content of the extender can be suitably determined corresponding to the type of extender used, type of colorant used and so on, in general, it is preferably about 1 to 30% by weight, and particularly preferably 2 to 20% by weight, of the composition of the present invention.

Any solvent can be used for a solvent able to be used in the present invention provided it is normally used in ink compositions for printing, writing and so on. Examples of solvents which can be used include alcohols or polyatomic alcohols, esters, ethers, ketones, hydrocarbons and glycol ethers, and these solvents may be suitably selected corresponding to the solubility of the dye or resin binder used.

Although the solvent content can be suitably determined corresponding to the type of solvent used, type of colorant used and so on, in general, it is preferably about from 40 to 95% by weight, and particularly preferably from 60 to 90% by weight, of the composition of the present invention.

Each of these components may be blended simultaneously or sequentially, and uniformly mixed by using a known agitation device such as a homogenizer or dissolver. For example, the above-mentioned solvent and, as necessary, cationic surfactant, resin binder and extender, may be sequentially blended into a solvent followed by mixing and stirring with an agitation device.

(2) Hydrogen Peroxide Plasma Sterilization Detection Indicator

An indicator of the present invention contains a color changing layer composed of the above-mentioned ink composition of the present invention. In general, the color changing layer can be formed by coating or printing the ink composition of the present invention on a base material. There are no particular limitations on the base material provided it allows the formation of the color changing layer, examples of which include metal or alloy, ceramics, glass, concrete, plastic (such as polyethylene terephthalate (PET), polypropylene, Nylon or polystyrene), textiles (such as non-woven fabric, woven fabric and other fiber sheets) and compound materials thereof. In addition, synthetic resin fiber paper such as synthetic polypropylene paper and synthetic polyethylene paper (synthetic paper) can also be used preferably.

The color changing layer in the present invention includes not only that in which the color thereof changes to another color, but also that in which the color fades or disappears.

Formation of the color changing layer can be carried out in accordance with known printing methods such as silk screen printing, gravure printing, offset printing, relief printing and flexography using the ink composition of the present invention. In addition, the color changing layer can also be formed by a method other than printing. For example, the color changing layer can be formed by immersing a base material in the ink composition. This is particularly suitable for ink-penetrable materials such as non-woven fabric.

The color changing layer preferably has a plurality of cracks in the surface thereof. Namely, the color changing layer is preferably porous as a result of having open pores formed in the surface thereof. As a result of having this structure, the sensitivity of hydrogen peroxide plasma sterilization detection can be further enhanced. In this case, a desired color changing effect is obtained even if the color changing layer is arranged within a pouch or bag for hydrogen peroxide plasma sterilization. Cracks can be formed particularly effectively by using a cellulose resin for the binder of the ink composition of the present invention. Namely, the use of a cellulose resin makes it possible to form the above-mentioned cracks while maintaining satisfactory fixation.

In the present invention, a non-color changing layer which does not change color in a hydrogen peroxide plasma sterilization atmosphere may also be formed on the base material and/or color changing layer. The non-color changing layer can normally be formed from commercially available ordinary colored ink. For example, water-based ink, oil-based ink or non-solvent ink can be used. Components such as resin binders, extenders and solvents blended into known inks may also be contained in the ink used to form the non-color changing layer.

Formation of the non-color changing layer may be carried out in the same manner as in the case of the color changing layer. For example, the non-color changing layer can be formed in accordance with known printing methods such as silk screen printing, gravure printing, offset printing, relief printing and flexography using ordinary colored ink. Furthermore, there are no particular limitations on the order in which the color changing layer and non-color changing layer are printed, and the order may be suitably selected corresponding to the printed design and so on.

The indicator of the present invention may also comprise a colored layer which changes color in a hydrogen peroxide atmosphere. In this case, the colored layer and the color changing layer may be formed so as to be mutually overlapping, or may be formed so as not to be mutually overlapping in the form of lines or spots.

By respectively forming on a support a layer which changes color only in the hydrogen peroxide filling process prior to plasma generation, and a layer which changes color only in the process in which plasma is generated from the hydrogen peroxide, it is possible to detect whether or not both processes have been carried out properly during sterilization work. In addition, if both layers are respectively formed at different locations on a support, each process can be confirmed on the same support.

In the case of having formed both layers overlapping on a support, each process can be detected in the form of a two-stage color change. For example, in the case of forming a layer which changes from red to yellow when contacted by hydrogen peroxide, and a layer which changes from blue to colorless in an atmosphere in which plasma has been generated from hydrogen peroxide, the indicator is violet in the untreated state, and yellow following proper sterilization. In the case hydrogen peroxide plasma has not been generated after the hydrogen peroxide has been filled, the indicator demonstrates a green color of the state in which blue and yellow are mixed. As a result, an indicator of this configuration changes from violet to green to yellow in that order in the case it has gone through the proper sterilization process. In the case the indicator is yellow following sterilization, this indicates that the proper sterilization process has been carried out, while in the case it is green, indicates that an abnormality has occurred in the generation of hydrogen peroxide plasma, and if it remains violet, indicates that an abnormality has occurred in filling of hydrogen peroxide into the sterilization vessel.

In the case of forming two layers overlapping on a support, if the transparency of both layers is inadequate, a dark color tone frequently results due to subtractive color mixing. If a large number of both layers are formed by positioning adjacent to each other on straight lines, curved lines or spots so as not to mutually overlap, subtractive color mixing does not occur and color tones become vivid, thereby resulting in a more preferable form of indicator in terms of visibility.

In the case of forming a large number of both layers by positioning adjacent to each other on straight lines, curved lines or spots so as not to mutually overlap, the color tone of the indicator can be finely adjusted to a design offering better visibility by regulating the thickness of the lines and spots or by creating a difference in the formation frequency of one layer relative to the multiple layers.

As was previously described in the literature of the prior art, a layer which changes color only in the hydrogen peroxide filling process can be formed on a support by means such as coating or printing using a composition which comprises a so-called pH indicator as the colorant, and a component capable of forming an alkaline environment.

A layer which does not change color due to contact by hydrogen peroxide alone, but rather changes color only when contacted by hydrogen peroxide plasma can be formed on a support by means such as coating or printing from a composition comprising a colorant such as an anthraquinone dye, methine dye or azo dye together with a quaternary ammonium salt. This was proposed by the inventors of the present invention as Japanese Patent Application Publication No. 2001-174449 and Japanese Patent Application No. 2004-101035.

In the indicator of the present invention, one layer each of the color changing layer and the non-color changing layer may be formed, or multiple layers of each may be formed. In addition, multiple color changing layers may be laminated together or multiple non-color changing layers may be laminated together. In this case, the laminated color changing layers may have the same or different compositions. Similarly, multiply laminated non-color changing layers may also have the same or different compositions.

Moreover, the color changing layer and the non-color changing layer may be formed entirely or partially over the surface of the base material or each layer. In these cases, it is preferable that the color changing layer and non-color changing layer be formed so that a portion or all of at least one color changing layer is exposed to the plasma sterilization treatment atmosphere to ensure that the color of the color changing layer changes in particular.

In the present invention, the color changing layer and the non-color changing layer may be combined in any manner provided completion of plasma sterilization treatment is able to be confirmed. For example, the color changing layer and non-color changing layer may be formed so that the color difference between the color changing layer and non-color changing layer only be able to be distinguished by a color change of the color changing layer, or they may be formed so that the color difference between the color changing layer and non-color changing layer only disappears when the color of the color changing layer changes. In the present invention, the color changing layer and the non-color changing layer are preferably formed so that the color difference between them can only be distinguished by a color change of the color changing layer.

In the case of allowing a color difference to be distinguished, the color changing layer and non-color changing layer may be formed so that, for example, at least one type of character, pattern or symbol appears when the color changing layer changes color. In the present invention, characters, patterns and symbols include all information indicating that color has changed. These characters and so on may be suitably designed corresponding to the purpose of use and so on.

In addition, mutually different colors may be used for the color changing layer and non-color changing layer prior to changing color. For example, both layers may be made to have substantially the same color, and the color difference (contrast) between the color changing layer and non-color changing layer may be allowed to be distinguished only after the color has changed.

In the indicator of the present invention, the color changing layer and non-color changing layer can be formed so that they do not overlap. As a result, the amount of ink used can be conserved.

Moreover, in the present invention, a color changing layer or non-color changing layer may be additionally formed on at least one of the color changing layer and non-color changing layer. For example, if a color changing layer having a different design is further formed on a layer in which a color changing layer and non-color changing layer are formed so as not to overlap (color changing-non-color changing layer), since a state can be created in which the boundary between the color changing layer and non-color changing layer in the color changing-non-color changing layer cannot be substantially distinguished, more superior design properties can be achieved.

The indicator of the present invention can be applied to any plasma sterilization treatment provided it is carried out in a hydrogen peroxide atmosphere. Thus, it is useful as an indicator in a plasma sterilization treatment device (more specifically, a device which carried out sterilization by generating plasma in a hydrogen peroxide or other oxidizing gas atmosphere). For example, when using this indicator, it is exposed to a plasma sterilization treatment atmosphere together with instruments or the like subjected to sterilization treatment by placing the indicator of the present invention in a commercially available plasma sterilization device. In this case, a predetermined plasma sterilization treatment can be determined to have been carried out by a color change of the indicator placed in the device.

(3) Pouch

The present invention includes a pouch or bag for hydrogen peroxide plasma sterilization provided with an indicator of the present invention on an inner surface of a gas-permeable pouch.

The gas-permeable pouch is preferably a pouch which enables hydrogen peroxide plasma sterilization to be carried out with a treated material sealed inside. A known or commercially available pouch used as a plasma sterilization pouch can be used. For example, a pouch formed from polyethylene fibers (synthetic polyethylene paper) can be used preferably. After placing a treated material in this pouch and sealing the opening by heat sealing and so on, the entire pouch with the treated material inside can be treated in a sterilization treatment device.

The indicator of the present invention may be arranged on an inner surface of the above-mentioned pouch. There are no limitations on the method by which the indicator is arranged, and in addition to the use of an adhesive or heat sealing, the indicator can be formed by coating or printing the ink composition of the present invention directly onto an inner surface of the pouch. In addition, in the case of coating or printing as described above, the indicator can be formed in the production stage of the pouch.

In a pouch of the present invention, a transparent window is preferably provided in a portion of the pouch so as to allow visual confirmation of the indicator from the outside. For example, the pouch may be produced from a transparent sheet and the above-mentioned synthetic polyethylene paper, and the indicator may be formed on an inner surface inside the pouch at a location such that it is visible through the transparent sheet.

In the case of sterilization treatment using a pouch of the present invention, a method may be employed comprising the steps of, for example, loading a treated material into the pouch, sealing the pouch with the treated material loaded inside, and placing the pouch in a hydrogen peroxide plasma sterilization atmosphere. More specifically, after placing a treated material (such as a medical instrument or food) in the pouch, the pouch is sealed in accordance with a known method such as heat sealing. Next, the entire pouch with the treated material inside is arranged in a hydrogen peroxide plasma sterilization atmosphere. Sterilization treatment is then carried out by, for example, arranging the pouch in a sterilization chamber of a known or commercially available plasma sterilization device (low-temperature plasma sterilization system). Following completion of sterilization treatment, the entire pouch is taken out and the treated material can be stored in the pouch until the time of use. In this case, the pouch is preferably placed in a hydrogen peroxide plasma sterilization atmosphere until the color changing layer of the indicator changes color.

EXAMPLE

The following further clarifies the characteristics of the present invention by indicating examples thereof. Furthermore, the present invention is not limited to these examples.

Examples 1-1 to 1-18

Inks were prepared using the components indicated in Table 1. More specifically, after stirring and mixing a solvent, dye and resin with a dissolver, a non-color changing colorant (when required) and resin binder were added followed by additional stirring. Finally, a cationic surfactant and extender were added and mixed to obtain an ink.

TABLE 1

| Composition | Example 1 | 2 | 3 | 4 | 5 | 6 | 7 | 8 | 9 |
|---|---|---|---|---|---|---|---|---|---|
| C.I. Basic Red 14 | 0.5 | | | | | | | | |
| C.I. Basic Violet 7 | | 0.5 | | | | | 0.5 | | |
| C.I. Disperse Orange 13 | | | 0.5 | | | | | | 0.5 |
| C.I. Basic Blue 9 | | | | 0.5 | | | | 0.5 | |
| C.I. Solvent Violet 8 | | | | | 0.5 | 0.5 | | | |
| C.I. Solvent Blue 14 | | | | | | | | | |
| Microlith Green G-T | | | | | | | | 2.0 | |
| Microlith Yellow 3R-T | | | | | | | | | |
| Bersamide 756 | 10.0 | 10.0 | 10.0 | 10.0 | 10.0 | 10.0 | | | |
| Johncryl 690 | | | | | | | 10.0 | | 10.0 |
| Denka Butyral #2000-L | | | | | | | | 10.0 | 5.0 |
| Nitrocellulose RS1/2 | | | | | | | | | |
| Nikkol CA-2150 | 1.0 | 1.0 | 1.0 | 1.0 | 1.0 | 1.0 | | 1.0 | |
| Nikkol CA-2465 | | | | | | | 1.0 | | 1.0 |
| Lauryl isoquinolinium bromide | | | | | | | | | |
| 2-chloro-1,3-dimethyl imidazolinium chloride | | | | | | | | | |
| Cetyl pyridinium chloride | | | | | | | | | |
| Aerosil R-972 | | | | | | 5.0 | 5.0 | | 5.0 |
| Butyl cellusorb | 68.5 | 68.5 | 68.5 | 68.5 | 68.5 | 61.5 | 61.5 | 68.5 | 58.5 |
| Cyclohexanone | 20.0 | 20.0 | 20.0 | 20.0 | 20.0 | 20.0 | 20.0 | 20.0 | 20.0 |
| Total | 100.0 | 100.0 | 100.0 | 100.0 | 100.0 | 100.0 | 100.0 | 100.0 | 100.0 |
| Effect | | | | | | | | | |
| Test Example 1 | Red → No color | Red → No color | Orange → No color | Blue → No color | Violet → No color | Russet → Yellow | Russet → Green | Blue → No color | Orange → No color |
| Test Example 2 | Red → No color | Red → No color | Orange → No color | Blue → No color | Violet → No color | Russet → Yellow | Russet → Green | Blue → No color | Orange → No color |

| Composition | Example 10 | 11 | 12 | 13 | 14 | 15 | 16 | 17 | 18 |
|---|---|---|---|---|---|---|---|---|---|
| C.I. Basic Red 14 | | | | | | | | | |
| C.I. Basic Violet 7 | | 0.5 | 0.5 | 0.5 | 0.5 | 0.5 | | | |
| C.I. Disperse Orange 13 | | | | | | | | | |
| C.I. Basic Blue 9 | 0.5 | | | | | | | | |
| C.I. Solvent Violet 8 | | | | | | | 0.5 | 0.5 | |
| C.I. Solvent Blue 14 | | | | | | | | | 0.5 |
| Microlith Green G-T | | | | | | | | | |
| Microlith Yellow 3R-T | | | | | | | | | |
| Bersamide 756 | | 10.0 | 10.0 | 10.0 | | | | | |
| Johncryl 690 | | | | | 10.0 | 10.0 | 20.0 | 20.0 | 20.0 |
| Denka Butyral #2000-L | 10.0 | | | | | | | | |
| Nitrocellulose RS1/2 | 5.0 | | | | | | | | |
| Nikkol CA-1250 | 1.0 | | | | | | | | 1.0 |
| Nikkol CA-2465 | | | | | 1.0 | | | | |
| Lauryl isoquinolinium bromide | | 1.0 | | | | 1.0 | | | |
| 2-chloro-1,3-dimethyl imidazolinium chloride | | | 1.0 | | | | 1.0 | | |
| Cetyl pridinium chloride | | | | 1.0 | | | | 1.0 | |
| Aerosil R-972 | 5.0 | | | | 5.0 | 5.0 | 5.0 | 5.0 | 5.0 |
| Butyl cellusorb | 58.5 | 68.5 | 68.5 | 68.5 | 63.5 | 63.5 | 53.5 | 53.5 | 52.5 |
| Cyclohexanone | 20.0 | 20.0 | 20.0 | 20.0 | 20.0 | 20.0 | 20.0 | 20.0 | 21.0 |
| Total | 100.0 | 100.0 | 100.0 | 100.0 | 100.0 | 100.0 | 100.0 | 100.0 | 100.0 |
| Effect | | | | | | | | | |
| Test Example 1 | Blue → No color | Red → No color | Red → No color | Red → No color | Red → No color | Red → No color | Violet → No color | Violet → No color | Violet → No color |
| Test Example 2 | Blue → No color | Red → No color | Red → No color | Red → No color | Red → No color | Red → No color | Violet → No color | Violet → No color | Violet → No color |

Furthermore, detailed descriptions of the components shown in Table 1 are described below.

\* Dyes
   C.I. Basic Red 14: Methine dye
   C.I. Basic Violet 7: Azo dye
   C.I. Disperse Orange 13: Azo dye
   C.I. Basic Blue 9: Thiazine dye
   C.I. Solvent Violet 8: Triarylmethane dye
   C.I. Solvent Blue 14: Anthraquinone dye
(2) Non-Color Changing Colorants
   Microlith Green G-T (Ciba Specialty Chemicals)
   Microlith Yellow 3R-T (Ciba Specialty Chemicals)

(3) Binder Resins
  Bersamide 756 (Cognis Japan)
  Johncryl 690 (Johnson Polymer, styrene acrylic acid resin)
  Denka Butyral #2000-L (Denka Kagaku Kogyo, polyvinyl butyral)
  Nitrocellulose RS1/2 (Daicel Chemical Industries, nitrocellulose)
(4) Cationic Surfactants
  Nikkol CA-2150 (Nikko Chemicals)
  Nikkol CA-2465 (Nikko Chemicals)
  Lauryl isoquinolinium chloride (Wako Pure Chemical Industries, reagent)
  2-chloro-1,3-dimethylimidazolinium chloride (Wako Pure Chemical Industries, reagent)
  Cetyl pyridinium chloride (Wako Pure Chemical Industries, reagent)
(5) Extender
  Aerosil R-972 (Nippon Aerosil)
(6) Solvents
  Butyl cellusorb
  Cyclohexanone Test Example 1-1

The color changing properties of the ink compositions obtained in each example in response to ozone were investigated. Each ink composition was printed onto a PET film by silk screen printing (350 mesh). The printed film was exposed to ozone under conditions of a CT value of 1000 ppm·min with an ozone generator. The change in color of the samples following treatment were observed visually. The results are shown in Table 1.

Test Example 1-2

The color changing properties of the ink compositions obtained in each example in response to hydrogen peroxide gas were investigated. Each ink composition was printed onto a PET film by silk screen printing (350 mesh). Hydrogen peroxide was dropped into each film at 18000 ppm·min in a sealed container under reduced pressure at 40° C., and printed film was exposed to that atmosphere. The change in color of the samples following exposure were observed visually. The results are shown in Table 1.

Examples 2-1 to 2-18

Ink compositions were prepared by uniformly mixing each of the components indicated in Tables 2 and 3 with an agitator. More specifically, a solvent, dye and polyamide resin were first stirred and mixed with a dissolver. The mixture was heated as necessary in cases of difficulty in dissolving the polyamide resin. Next, a non-color changing pigment and resin binder were added followed by additional stirring, and a surfactant and extender were added after returning to normal temperature followed by uniform stirring to obtain an ink composition.

Comparative Examples 2-1 to 2-7

Ink compositions were prepared in the same manner as Example 1 with the exception of changing the ink compositions as indicated in Table 2.

TABLE 2

| Composition | Example | | | | | | | |
| --- | --- | --- | --- | --- | --- | --- | --- | --- |
|  | 1 | 2 | 3 | 4 | 5 | 6 | 7 | 8 |
| C.I. Disperse Violet 1 | 0.5 |  |  |  |  |  |  | 0.5 |
| C.I. Solvent Blue 35 |  | 0.5 |  |  |  |  |  |  |
| C.I. Disperse Red 4 |  |  | 0.5 |  |  |  |  |  |
| C.I. Solvent Red 1 |  |  |  | 0.5 |  |  |  |  |
| C.I. Solvent Red 23 |  |  |  |  | 0.5 |  |  |  |
| C.I. Disperse Red 58 |  |  |  |  |  | 0.5 |  |  |
| C.I. Basic Red 12 |  |  |  |  |  |  | 0.5 |  |
| Microlith Yellow 3R-T |  |  |  |  |  |  |  |  |
| Microlith Green G-T |  |  |  |  |  |  |  |  |
| Bersamide 756 | 10.0 | 10.0 | 10.0 | 10.0 | 10.0 | 10.0 | 10.0 | 10.0 |
| Vylon 200 |  |  |  |  |  |  |  |  |
| FQRS1/2 |  |  |  |  |  |  |  |  |
| Nikkol CA-1250 | 2.0 | 2.0 | 2.0 | 2.0 | 2.0 | 2.0 | 2.0 |  |
| Cation M2-100 |  |  |  |  |  |  |  | 2.0 |
| Lauryl isoquinolinium bromide |  |  |  |  |  |  |  |  |
| 2-chloro-1,3-dimethyl imidazolinium chloride |  |  |  |  |  |  |  |  |
| Cetyl pyridinium chloride |  |  |  |  |  |  |  |  |
| Aerosil R-972 | 5.0 | 5.0 | 5.0 | 5.0 | 5.0 | 5.0 | 5.0 | 5.0 |
| Butyl cellusorb | 58.0 | 58.0 | 58.0 | 58.0 | 58.0 | 58.0 | 58.0 | 58.0 |
| Cyclohexanone | 24.5 | 24.5 | 24.5 | 24.5 | 24.5 | 24.5 | 24.5 | 24.5 |
| Total | 100.0 | 100.0 | 100.0 | 100.0 | 100.0 | 100.0 | 100.0 | 100.0 |
| Color change (visual) | Mauve → No color | Blue → No color | Red → No color | Red → No color | Red → No color | Red → No color | Red → No color | Mauve → No color |
| Color difference before and after sterilization ΔE* | 48 | 40 | 41 | 43 | 40 | 43 | 46 | 46 |
| Adhesion (cross-cut) (score) | 8 | 8 | 8 | 8 | 8 | 8 | 8 | 8 |

| Composition | Comparative Example | | | | | | |
| --- | --- | --- | --- | --- | --- | --- | --- |
|  | 1 | 2 | 3 | 4 | 5 | 6 | 7 |
| C.I. Disperse Violet 1 | 0.5 | 0.5 | 0.5 | 0.5 | 0.5 |  |  |
| C.I. Solvent Blue 35 |  |  |  |  |  |  |  |
| C.I. Disperse Red 4 |  |  |  |  |  |  |  |

TABLE 2-continued

| | | | | | | | | |
|---|---|---|---|---|---|---|---|---|
| C.I. Solvent Red 1 | | | | | | 0.5 | | |
| C.I. Solvent Red 23 | | | | | | | | |
| C.I. Disperse Red 58 | | | | | | | | |
| C.I. Basic Red 12 | | | | | | | 0.5 | |
| Microlith Yellow 3R-T | | | | | | | | |
| Microlith Green G-T | | | | | | | | |
| Bersamide 756 | | 10.0 | 10.0 | 10.0 | | | | |
| Vylon 200 | 10.0 | | | | 10.0 | 10.0 | 10.0 | |
| FQRS1/2 | | | | | | | | |
| Nikkol CA-1250 | | | 2.0 | | 2.0 | 2.0 | 2.0 | |
| Cation M2-100 | | | | | | | | |
| Lauryl isoquinolinium bromide | | | | | | | | |
| 2-chloro-1-3-dimethyl imidazolinium chloride | | | | | | | | |
| Cetyl pyridinium chloride | | | | | | | | |
| Aerosil R-972 | | | | 5.0 | 5.0 | 5.0 | 5.0 | |
| Butyl cellusorb | | 65.0 | 63.0 | 60.0 | | | | |
| Cyclohexanone | 89.5 | 24.5 | 24.5 | 24.5 | 82.5 | 82.5 | 82.5 | |
| Total | 100.0 | 100.0 | 100.0 | 100.0 | 100.0 | 100.0 | 100 | |
| Color change (visual) | Mauve → Mauve | Mauve → Mauve | Mauve → Mauve | Mauve → Mauve | Mauve → Mauve | Red → Pink | Red → Pink | |
| Color difference before and after sterilization ΔE* | 2 | 24 | 23 | 26 | 15 | 10 | 12 | |
| Adhesion (cross-cut) (score) | 10 | 10 | 10 | 8 | 8 | 8 | 8 | |

TABLE 3

| Composition | Example | | | | | | | | | |
|---|---|---|---|---|---|---|---|---|---|---|
| | 9 | 10 | 11 | 12 | 13 | 14 | 15 | 16 | 17 | 18 |
| C.I. Disperse Violet 1 | 0.5 | | | | 0.5 | 0.5 | 0.5 | | | |
| C.I. Solvent Blue 35 | | | | | | | | | | |
| C.I. Disperse Red 4 | | 1.0 | | | | | | 1.0 | | |
| C.I. Solvent Red 1 | | | | | | | | | | |
| C.I. Solvent Red 23 | | | 1.0 | | | | | | 1.0 | |
| C.I. Disperse Red 58 | | | | | | | | | | |
| C.I. Basic Red 12 | | | | 1.0 | | | | | | 1.0 |
| Microlith Yellow 3R-T | 3.0 | | | | | | | | | |
| Microlith Green G-T | | 3.0 | 3.0 | 3.0 | | | | 3.0 | 3.0 | 3.0 |
| Bersamide 756 | 5.0 | 5.0 | 5.0 | 5.0 | 10.0 | 10.0 | 10.0 | 5.0 | 5.0 | 5.0 |
| Vylon 200 | | | | | | | | | | |
| FQRS1/2 | 5.0 | 5.0 | 5.0 | 5.0 | | | | 5.0 | 5.0 | 5.0 |
| Nikkol CA-1250 | | | | | | | | | | |
| Cation M2-100 | 4.0 | 4.0 | 4.0 | 4.0 | | | | 4.0 | | |
| Lauryl isoquinolinium bromide | | | | | 2.0 | | | | 4.0 | |
| 2-chloro-1-3-dimethyl imidazolinium chloride | | | | | | 2.0 | | | | 4.0 |
| Cetyl pyridinium chloride | | | | | | | 2.0 | | | 4.0 |
| Aerosil R-972 | 5.0 | 5.0 | 5.0 | 5.0 | 5.0 | 5.0 | 5.0 | 5.0 | 5.0 | 5.0 |
| Butyl cellusorb | 53.0 | 52.5 | 62.5 | 52.5 | 58.5 | 58.0 | 58.0 | 52.5 | 52.5 | 52.5 |
| Cyclohexanone | 24.5 | 24.5 | 24.5 | 24.5 | 24.5 | 24.5 | 24.5 | 24.5 | 24.5 | 24.5 |
| Total | 100.0 | 100.0 | 100.0 | 100.0 | 100.0 | 100.0 | 100.0 | 100.0 | 100.0 | 100.0 |
| Color change (visual) | Brown → Yellow | Mauve → Green | Mauve → Green | Mauve → Green | Mauve → No color | Mauve → No color | Mauve → No color | Mauve → Green | Mauve → Green | Mauve → Green |
| Color difference before and after sterilization ΔE* | 40 | 42 | 45 | 43 | 44 | 45 | 43 | 40 | 41 | 42 |
| Adhesion (cross-cut) (score) | 10 | 10 | 10 | 10 | 8 | 8 | 10 | 10 | 10 | 10 |

Furthermore, detailed descriptions of the components shown in Tables 2 and 3 are described below.

1) C.I. Disperse Violet 1: Anthraquinone dye
2) C. I. Solvent Blue 35: Anthraquinone dye
3) C.I. Disperse Red 4: Anthraquinone dye
4) C.I. Solvent Red 1: Azo dye
5) C.I. Solvent Red 23: Disazo dye
6) C.I. Disperse Red 58: Thiazole azo dye
7) C.I. Basic Red 12: Methine dye
8) Microlith Yellow 3R-T: Non-color changing pigment, product name "Microlith Yellow 3R-T" (Ciba Specialty Chemicals)
9) Microlith Green G-T: Non-color changing pigment, product name "Monolith Green G-T" (Ciba Specialty Chemicals)
10) Bersamide 756: Polyamide resin, product name "Bersamide 756" (Cognis Japan)
11) Vylon 200: Polyester resin, product name "Vylon 200" (Toyobo)

12) FQRS1/2: Cellulose resin binder, product name "Nitrocellulose FQRS1/2" (Daicel Chemical Industries)
13) Nikkol CA-2150: Quaternary ammonium salt surfactant, product name "NIKKOL CA-2150" (Nikko Chemicals)
14) Cation M2-100: Quaternary ammonium salt surfactant, product name "Cation M2-100" (Nikko Chemicals)
15) Lauryl isoquinolinium chloride: Cationic surfactant (Wako Pure Chemical Industries, reagent)
16) 2-chloro-1,3-dimethylimidazolinium chloride: Cationic surfactant (Wako Pure Chemical Industries, reagent)
17) Cetyl pyridinium chloride: Cationic surfactant (Wako Pure Chemical Industries, reagent)
18) Aerosil R-972: Silica gel, product name "Aerosil R-972" (Nippon Aerosil)
19) Butyl cellusorb: Solvent
20) Cyclohexanone: Solvent Test Example 2-1

The color changing properties and adhesion of each of the ink compositions of the examples and comparative examples were investigated. Samples were prepared by forming a film using the ink composition onto PET paper (size: 50 mm×50 mm) with a 350 mesh silk screen printer followed by allowing to dry completely.

Color changing properties were investigated by placing a sample in a pouch (sterile pouch, product name "Sterrad Sterile Pouch Regular"), the opening of which was sealed by heat sealing, placing the pouch containing the sample in a plasma sterilizer device (low-temperature plasma sterilization system "Sterrad 50", Johnson & Johnson Medical, using hydrogen peroxide gas), carrying out sterilization under standard conditions, and investigating the degree of color change both visually and with a color difference meter (product name "CR-300", Minolta). The results are shown in Tables 2 and 3.

Adhesion was investigated by conducting a test complying with "JIS K5400 General Paint Film Test Methods, 8.5.2 Cross-cut test" on the sample coated films. The results are shown in Tables 2 and 3.

Test Example 2-2

Figure 2:
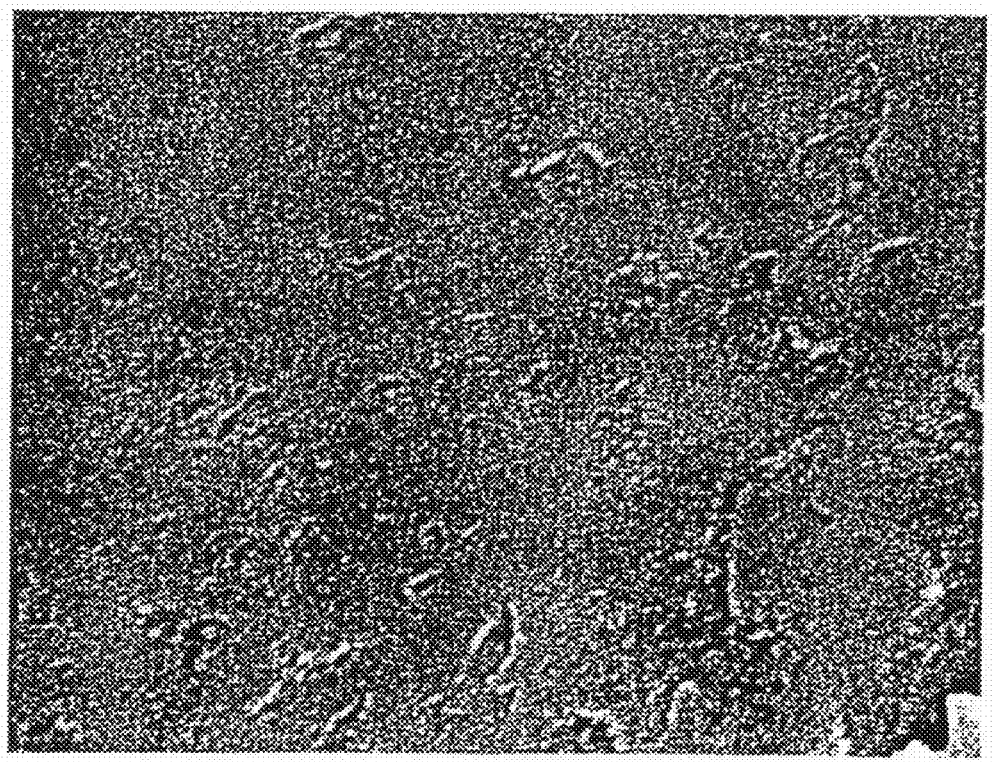
FIG. 2 is a photograph showing the results of observing a surface coated with the ink composition of Comparative Example 1 with a scanning electron microscope.

When coated films of samples of examples used in Test Example 2-1 were measured with a scanning electron microscope, a large number of cracks were confirmed to be present having a width of about 0.3 to 3 µm. The result of observing the coated film of Example 2-1 is shown in FIG. 1 (image). In addition, the result of similarly observing the coated film of Comparative Example 2-1 is shown in FIG. 2 (image).

Example 3-1

Preparation of Ink Composition 10 g of pH indicator (triammonium aurintricarboxylate), 1 g of anthraquinone dye ("Miketon Fast Violet R", Mitsui Toatsu Chemicals), 2.0 g of quaternary ammonium salt ("Nikkol CA-2150", Nikko Chemicals), 10 g of resin binder ("Bersamide 756", Cognis Japan) and 10 g of extender ("Aerosil R-972", Nippon Aerosil) were stirred in 150 g of ethyl cellusorb followed by dissolving and dispersing to obtain Composition A.

Example 3-2

Production of Indicator Sheet

Using Composition A, a circle having a diameter of 1 cm was printed onto a white PET sheet with a 350 mesh screen and the coat was dried. As a result, Indicator B was obtained having a violet printed layer on a white background.

Example 3-3

Confirmation of Degree of Color Change of Indicator During Exposure to Hydrogen Peroxide Indicator B was placed in 1 liter desiccator and the following procedure was repeated twice. Namely, after reducing the pressure in the desiccator to 0.5 torr while maintaining at 45° C., 18 µL of 58% hydrogen peroxide were introduced into the desiccator with a microsyringe. After repeating this procedure twice, the degree of color change of Indicator B was observed.

The above-mentioned treatment was carried out under the conditions of the "Sterrad 100S" hydrogen peroxide low-temperature plasma sterilizer (Johnson & Johnson).

Before and after treatment, the indicator changed from violet to green. Since the pH indicator (triammonium aurintricarboxylate) changes from red to yellow when contacted with the hydrogen peroxide, and the anthraquinone dye ("Miketon Fast Violet R", Mitsui Toatsu Chemicals) changes from violet to no color when contacted with hydrogen peroxide plasma, in this example, only the pH indicator changed in color, resulting in a maroon color consisting of a mixture of yellow and purple.

Example 3-4

Confirmation of Degree of Color Change of Indicator During Hydrogen Peroxide Low-Temperature Plasma Sterilization Treatment Indicator B was placed in the sterilizing layer of the "Sterrad 100S" hydrogen peroxide low-temperature sterilizer (Johnson & Johnson), the sterilizer was set to a short cycle, and sterilization treatment was carried out once.

Before and after treatment, the indicator changed from violet to yellow. Both the pH indicator and anthraquinone dye changed color, resulting in a mixed color of yellow and no color.

Example 3-5

Indicator B was subjected to no treatment, treatment with hydrogen peroxide only (Example 3-3) and sterilization treatment with hydrogen peroxide plasma (Example 3-4) to visually confirm differences in visibility. As a result, differences which were able to be distinguished at a glance were observed between no treatment, after treatment with hydrogen peroxide only, and after sterilization treatment with hydrogen peroxide plasma.

Thus, according to the present invention, a chemical indicator is able to be provided which makes it possible to easily distinguish whether or not both the process of introducing hydrogen peroxide of plasma sterilization treatment and the process of generating plasma from the hydrogen peroxide have been carried out properly before and after sterilization.

Example 4-1

Preparation of Composition a Changing Color Only During a Hydrogen Peroxide Filling Step 14.3 g of triammonium aurintricarboxylate and 66.3 g of resin binder "Bersamide 756", Cognis Japan) were dissolved by stirring and mixing in 120.3 g of 2-propanol in accordance with Japanese Patent Application Publication No. 2001-13129 to obtain Composition A.

Preparation of Composition B Changing Color During Contact with Hydrogen Peroxide Plasma 0.2 g of anthraquinone dye ("Miketon Fast Violet R", Mitsui Toatsu Chemicals), 2.0 g of quaternary ammonium salt ("Nikkol CA-2150", Nikko Chemicals), 7.4 g of resin binder ("Ethocel 10", Dow Chemical) and 9.8 g of extender ("Aerosil R-972", Nippon Aerosil) were stirred, dissolved and dispersed in 80.7 g of ethyl cellusorb in accordance with Japanese Patent Application Publication No. 2001-174449 to obtain Composition B.

Example 4-2

Production of Indicator Sheet

Figure 3:
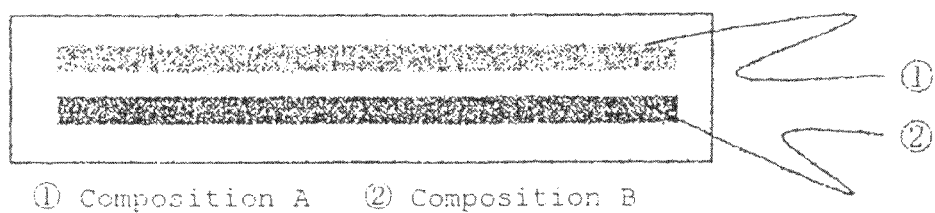
FIG. 3 is a schematic drawing of a simple example of a chemical indicator of the present invention.
Figure 4:
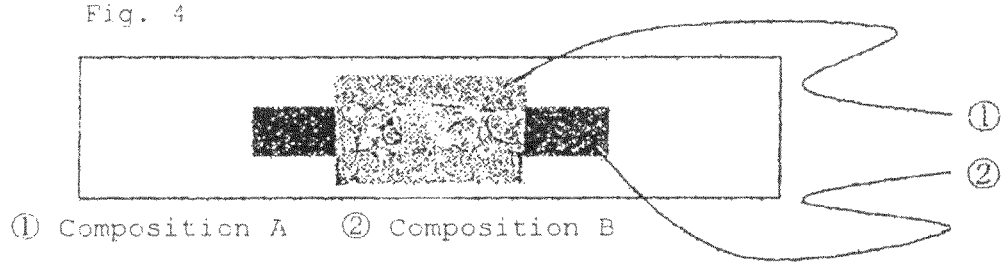
FIG. 4 is a schematic drawing of the case of composing a chemical indicator of the present invention by over-coating.
Figure 5:
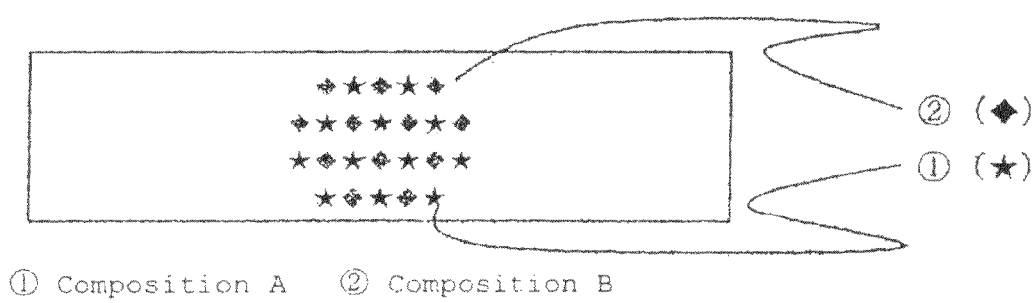
FIG. 5 is a schematic drawing of the case of composing a chemical indicator of the present invention in a spotted pattern.

Composition A and Composition B were screen printed on a white PET sheet with a 350 mesh screen to have the compositions shown in FIGS. 3 to 5 to produce Indicator C (FIG. 3), Indicator D (FIG. 4) and Indicator E (FIG. 5).

Example 4-3

Confirmation of Degree of Color Change of Indicators During Hydrogen Peroxide Exposure Indicators C, D and E were placed in a 1 liter desiccator and the following procedure was repeated twice. Namely, after reducing the pressure in the desiccator to 0.5 torr while maintaining at 45° C., 18 µL of 58% hydrogen peroxide were introduced into the desiccator with a microsyringe. After repeating this procedure twice, the degree of color change of Indicators C, D and E was observed.

The above-mentioned treatment was carried out in accordance with the conditions of the "Sterrad 100S" hydrogen peroxide low-temperature plasma sterilizer (Johnson & Johnson).

The colors of the indicators before and after treatment were as follows. In the case of Indicator C, only the portion of Composition A which was red changed to yellow, while the portion of Composition B remained violet before and after treatment. In the case of Indicator D, the overlapping portion of Compositions A and B which was dark violet changed to dark maroon. The portion of Composition A protruding from the overlapping portion became yellow, while the portion of Composition B remained violet before and after treatment. In the case of Indicator E, the overlapping portion of Composition A and B changed from an overall bright violet appearance to a yellow color only at the star-shaped ★portions of Composition A after treatment, while overall, Indicator E changed to a bright maroon appearance. At this time, the diamond-shaped ♦ portions of Composition B remained violet before and after treatment.

Example 4-4

Confirmation of Degree of Color Change of Indicators During Hydrogen Peroxide Low-Temperature Plasma Sterilization Treatment Indicators C, D and E were placed in the sterilizing layer of the "Sterrad 100S" hydrogen peroxide low-temperature sterilizer (Johnson & Johnson), the sterilizer was set to a short cycle, and sterilization treatment was carried out once.

The colors of the indicators before and after treatment were as follows. In the case of Indicator C, the portion of Composition A which was red changed to yellow, and the portion of Composition B which was violet became essentially colorless. In the case of Indicator D, the overlapping portion of Compositions A and B which was dark violet changed to dark yellow. The portion of Composition A protruding from the overlapping portion became yellow, and composition B became essentially colorless. In the case of Indicator E, the overlapping portion of Compositions A and B changed from a bright violet overall to a bright pale yellow color overall after treatment. The star-shaped ★portions of Composition A changed to yellow, while the diamond-shaped ♦ portions of Composition B became essentially colorless.

Example 4-5

Indicators C, D and E were subjected to no treatment, treatment with hydrogen peroxide only (Example 4-3) and sterilization treatment with hydrogen peroxide plasma (Example 4-4) to visually confirm differences invisibility. As a result, differences which were able to be distinguished at a glance were observed between no treatment, after treatment with hydrogen peroxide only, and after sterilization treatment with hydrogen peroxide plasma for each of Indicators C, D and E. In terms of hue, Indicators C and E were particularly satisfactory since they were able to be distinguished easily with bright colors.

Thus, according to the present invention, it was determined that it is possible to easily distinguish whether or not both the process of introducing hydrogen peroxide of plasma sterilization treatment and the process of generating plasma from the hydrogen peroxide have been carried out properly before and after sterilization.

The invention claimed is:

1. A method for detecting an ozone gas,
comprising a step of placing an ozone gas detection indicator in an ozone gas treatment device, and confirming a color difference in the indicator,
wherein the ozone gas detection indicator comprises a color changing layer for detecting an ozone gas formed of an ink composition that has a plurality of cracks in the surface of the color changing layer,
wherein the ink composition for detecting an ozone gas comprises
at least one selected from the group consisting of azo dye, methine dye and triarylmethane dye,
a nitrogen-containing polymer,
a resin binder, wherein all or a portion of the resin binder is a cellulose resin,
and
a cationic surfactant.

2. The method for detecting an ozone gas according to claim 1, wherein the cationic surfactant is at least one selected from the group consisting of an alkyl trimethyl ammonium salt, isoquinolinium salt, imidazolinium salt and pyridinium salt.

3. The method for detecting an ozone gas according to claim 1, wherein the ink composition further comprises at least one selected from the group consisting of extender and resin binder.

4. The method for detecting an ozone gas according to claim 1, wherein the ink composition further comprises at least one type of colorant which does not change color in an oxidizing gas atmosphere.

5. The method for detecting an ozone gas according to claim 1, wherein the ink composition further comprises an anthraquinone dye as a dye.

6. The method for detecting an ozone gas according to claim 1, wherein the ink composition further comprises a non-color changing layer which does not change color in an oxidizing gas atmosphere.

7. An indicator for detecting hydrogen peroxide plasma sterilization, comprising a color changing layer formed of an ink composition, which has a plurality of cracks in the surface of the color changing layer,
wherein the ink composition comprises:
1) at least one selected from the group consisting of azo dye and methine dye,
2) a nitrogen-containing polymer,
3) a cationic surfactant, and
4) a resin binder, wherein all or a portion of the resin binder is a cellulose resin.

8. The indicator according to claim 7, wherein all or a portion of the nitrogen-containing polymer is a polyamide resin.

9. The indicator according to claim 8, wherein the polyamide resin is a reaction product of a dimer of linoleic acid and a di- or polyamine.

10. The indicator according to claim 7, wherein the cationic surfactant is at least one selected from the group consisting of an alkyl trimethyl ammonium salt, isoquinolinium salt, imidazolinium salt and pyridinium salt.

11. The indicator according to claim 7, which further comprises an extender.

12. The indicator according to claim 11, wherein all or a portion of the extender is silica.

13. The indicator according to claim 7, wherein the content of the nitrogen-containing polymer is 1 to 20% by weight of the ink composition.

14. The indicator according to claim 7, which further comprises at least one type of colorant which does not change color in a plasma sterilization treatment atmosphere.

15. The indicator according to claim 7, which further comprises at least one type of component which changes color by reacting with hydrogen peroxide.

16. The indicator according to claim 15, wherein the component which changes color by reacting with hydrogen peroxide contains ammonium aurintricarboxylate.

17. The indicator according to claim 7, which further comprises at least one type of organic amine.

18. The indicator according to claim 7, which further comprises a non-color changing layer which does not change color in a plasma sterilization treatment atmosphere.

19. The indicator according to claim 7, which further comprises a colored layer which changes color in a hydrogen peroxide atmosphere.

20. The indicator according to claim 19, wherein the colored layer and the color changing layer are formed so as to be mutually overlapping.

21. The indicator according to claim 20, wherein the colored layer and the color changing layer are formed in a linear or spotted pattern so as not to be mutually overlapping.

22. A pouch for hydrogen peroxide plasma sterilization provided with the indicator according to claim 7 on an inner surface of a gas-permeable pouch.

23. The pouch according to claim 22, which is provided with a transparent window in a portion of the pouch so as to allow visual confirmation of the indicator from the outside.

24. The pouch according to claim 22, wherein the gas-permeable pouch is formed from polyethylene fibers.

25. A hydrogen peroxide plasma sterilization treatment method, comprising the steps of loading a treated material into the pouch according to claim 22, sealing the pouch with the treated material loaded therein, and placing the pouch in a hydrogen peroxide plasma sterilization atmosphere.

26. The method according to claim 25, wherein the pouch is placed in the hydrogen peroxide plasma sterilization atmosphere until the color changing layer of the indicator changes color.

27. A method for confirming hydrogen peroxide plasma sterilization treatment, comprising the steps of loading a treated material into the pouch according to claim 22, sealing the pouch with the treated material sealed therein, placing the pouch in a hydrogen peroxide plasma sterilization atmosphere, and confirming a color difference in the indicator of the pouch.

28. A method for detecting a hydrogen peroxide gas, comprising a step of placing a hydrogen peroxide gas detection indicator in a hydrogen peroxide gas treatment device, and confirming a color difference in the indicator,
wherein the hydrogen peroxide gas detection indicator comprises a color changing layer formed of an ink composition for detecting a hydrogen peroxide gas having a plurality of cracks in the surface of the color changing layer,
wherein the ink composition for detecting a hydrogen peroxide gas comprises
methine dye;
a nitrogen-containing polymer;
a resin binder, wherein all or a portion of the resin binder is a cellulose resin; and
a cationic surfactant.

* * * * *